United States Patent
Pfister et al.

(10) Patent No.: US 8,346,344 B2
(45) Date of Patent: Jan. 1, 2013

(54) DEVICE LOCALIZATION AND GUIDANCE

(75) Inventors: Marcus Pfister, Bubenreuth (DE); Laura Johnson, Boston, MA (US)

(73) Assignee: Siemens Aktiengesellschaft, Munich (DE)

(*) Notice: Subject to any disclaimer, the term of this patent is extended or adjusted under 35 U.S.C. 154(b) by 616 days.

(21) Appl. No.: 11/900,261

(22) Filed: Sep. 11, 2007

(65) Prior Publication Data

US 2009/0069672 A1 Mar. 12, 2009

(51) Int. Cl.
*A61B 5/05* (2006.01)

(52) U.S. Cl. ............ 600/424; 600/407; 378/42; 378/62; 378/87; 382/190; 382/192; 382/201; 382/203

(58) Field of Classification Search .................. 600/437, 600/407, 409, 410; 382/128
See application file for complete search history.

(56) References Cited

U.S. PATENT DOCUMENTS

| | | | | |
|---|---|---|---|---|
| 6,368,285 B1* | 4/2002 | Osadchy et al. | ............... | 600/508 |
| 6,725,079 B2* | 4/2004 | Zuk et al. | ...................... | 600/414 |
| 6,869,217 B2* | 3/2005 | Rasche et al. | ................. | 378/197 |
| 2008/0091101 A1* | 4/2008 | Velusamy et al. | ............ | 600/427 |

FOREIGN PATENT DOCUMENTS

DE 10 2005 012 985 A1 7/2006

OTHER PUBLICATIONS

U.S. Appl. No. 11/544,846, filed Oct. 5, 2006, Pfister.

Graeme Patrick P., *Registration of Tomographic Images to X-ray Projections for Use in Image Guided Interventions*, Dec. 1999, King's College London, GB, 203 pages.
Precision Planning, © 2007 CAS Innovations, obtained at Internet address: http://www.cas-innovations.de/cms/index.php?id=24&L=1, 1 page.
Precision in Therapy Planning and Navigation, © 2007 CAS Innovations, obtained at Internet address: http://www.cas-innovations.de/cms/index.php?id=43&L=1, 1 page.
Solutions for Surgery, © 2007 CAS Innovations, obtained at Internet address: http://www.cas-innovations.de/cms/index.php?id=4&L=1.
Successful Navigation, © 2007 CAS Innovations, obtained at Internet address: http://www.cas-innovations.de/cms/index.php?id=25&L=1, 1 page.

* cited by examiner

*Primary Examiner* — Tse Chen
*Assistant Examiner* — Joel F Brutus
(74) *Attorney, Agent, or Firm* — Lempia Summerfield Katz LLC (57) ABSTRACT

An apparatus and method is described for determining the location of a object inside a patient. Three dimensional image data of the patient is obtained by an imaging modality such as a C-arm X-ray device. The same or another imaging modality may be used to obtain projection radiographic images, having a coordinate system that can be registered with respect to that of the three dimensional image. The location of one or more features of a medical treatment device such as a needle or a catheter introduced into the imaging filed of view is determined either by an operator or by image analysis, in at least two projection radiographic images, and the position of the feature located in the three-dimensional volume. The projection on a radiographic image of a vector joining a first and a second position is used to assist in guiding the medical treatment device inside of the patient.

17 Claims, 9 Drawing Sheets

DEVICE LOCALIZATION AND GUIDANCE

TECHNICAL FIELD

The present application relates to an apparatus and method of localizing a device within a volume.

BACKGROUND

In medical imaging, image registration and fusion is now being used to align images from different modalities (or 2D and 3D images from the same modality) to bring additional information into the display of information from a modality. An example is the fusion of PET (positron emission tomography) or SPECT (single photon emission computed tomography) images showing tumor information, but little else, with CT (computed tomography), showing detailed anatomy. Another approach, which has gained attention lately, is 2D-3D registration: the registration of pre- or intraoperative 3D volume rendered data to intraoperatively acquired fluoroscopic or angiographic images.

One application of the registration technique is the navigation of a device, which can be visualized in the real-time 2D fluoroscopic image, using the information given by the 3D volumetric rendering, e.g. navigating a needle (seen in the fluoroscopic image) to a tumor (seen in the registered 3D volumetric image but not in the fluoroscopic image). However, the overlay of 2D and 3D images has no depth information so that navigation of a device may be difficult. The device can presently be navigated by viewing the device from several angles in fluoroscopic images. However, in addition to increasing the radiation does to the patient, this requires the movement of the C-arm of the X-ray device during the intervention.

SUMMARY

An apparatus for visualizing the position of an object is disclosed, including a first imaging modality capable of producing projection images from at least two orientations with respect to the object; a second imaging modality capable of producing three-dimensional images of a volume including the object; identifying a distinguishing feature on the object in the projection images taken from different orientations; and a processor configured to compute the location of the distinguishing feature in a three dimensional coordinate system using the identified distinguishing feature.

A method of guiding an object in a patient is described, the method including, providing a first imaging modality capable of obtaining three dimensional radiographic data; providing a second imaging modality capable of obtaining radiographic images of a patient or portion thereof from at least two orientations, the images of the second imaging modality being registered or registerable with the images of the first imaging modality; providing an image display device; introducing an object into the field of view of the second imaging modality; identifying at least one of first distinguishing feature of the object or a target in at least two radiographic images; determining the location of the at least one of the first distinguishing feature or the target in a three-dimensional coordinate system; and, displaying the location of the at least one of the first distinguishing or the target feature in at lest one radiographic image.

A software product is described, the product being recorded on machine readable media, that configures a computer to perform a method of visualizing guiding an object, the method including: obtaining three-dimensional imaging data of at least a portion of a patient; obtaining projection radiographic images of a volume including an object from at least two differing orientations; identifying a first distinguishing feature of an object, by one of displaying the radiographs or by automated image analysis; identifying at least one of a target location in the patient or a second distinguishing feature of the object; computing a vector between the first distinguishing feature and the second distinguishing feature or the target; and computing a projection of the vector for display on a fluoroscopic or radiographic image.

BRIEF DESCRIPTION OF THE DRAWINGS

FIG. 1 is (A) a first view of an imaging modality showing a first axis of radiation; and (B) a second view of the imaging modality showing the axis of radiation rotationally displaced by approximately 90°.

DETAILED DESCRIPTION

Exemplary embodiments may be better understood with reference to the drawings. Like numbered elements in the same or different drawings perform equivalent functions.

A system and method are described wherein a synthetic image of the tip, a portion of, or all of a device insertable into a patient, is oriented with respect to at least a 3D volumetric image of a portion of the patient. The data suitable for producing the 3D volumetric rendering of the morphology of the patient may be obtained by any of the imaging modalities known as capable of producing data satisfactory for 3-D medical images. The selection of the imaging modality device may be on the basis of the type of structure to be imaged, the characteristic of the structure to be imaged, and the like. The location of the medical or other device may be obtained by magnetic sensors, ultrasonic sensors, or by a fluoroscopic sensor. The fluoroscopic sensor may be the same as the 3D imaging sensor if, for example, a C-arm X-ray device is used to obtain the data for the 3D volumetric image rendering.

The position of the device with respect to the coordinate system of the 3D image may be determined by using, for example, projection radiographic images taken at substantially orthogonal orientations with respect to each other. The tip of a needle may be identified manually by an operator, or automatically by image recognition software algorithms. The projection of the needle in the two planes and the identification of the needle tip may serve to determine the position of the needle in the coordinate space of the 3D image, providing that the imaging modalities used for the 2D image acquisition and the 3D image acquisition have a known relative spatial relationship. For example, the same C-arm X-ray imaging modality may be used.

Where the same imaging modality is used to obtain both the 3D images and the 2D images, the relationship of the coordinate axes used to determine the needle location and the coordinate axes used for obtaining the 3D imaging data is known, and known coordinate transformations may be used to locate the position of the needle with respect to the 3D image. As such, a representation of the image may be fused with the 3D volumetric rendering of the patient, showing either the tip of the needle, or the tip of the needle and a sufficient portion of the needle to establish the directional orientation of the needle. Registration of images obtained by different devices is known in the art.

The 3D image may be from an image data set taken either pre-operatively or intraoperatively. The device location data images may also be taken interoperatively.

The 3D image may be viewed from any of the usual aspects as would be known in the art, and the fused representation of the needle shown in the various views as an integral part of the volumetric of fluoroscopic image.

In an aspect, the fused needle and volumetric data may be used to guide the needle to a target, for example, to a puncture point in an organ or structure. This may be accomplished by identifying the point of puncture in the 3D volumetric rendering, which may itself be a fusion of images from a plurality of modalities. The use of a plurality of volumetric or planar imaging modalities is known as useful in identifying tumors, or functionally evaluating such aspects as perfusion.

When a puncture point or target has been identified and designated in the 3D volumetric domain, a path may be computed between the tip of the needle and the designated puncture point. This may take into account the orientation of the needle, as previously determined. This path may be shown on the 3D image, or projections of the path shown in any 2D image, which may be an image used to assist in guiding he needle. Guidance of the needle may be manually, the motion being monitored by one or more fluoroscopic images providing for real-time monitoring. The actual position of the needle in the image may be compared with the generated image of the path to the puncture point. The direction and advancement of the needle may be adjusted if it deviates from the projected path, and the localization of the needle tip and direction may be repeated if necessary.

In an alternative, the needle may be guided by a robotic device, the coordinate system of which is also registered with respect to the 3D volumetric image. When a robotic guidance system is used, the path of the needle may be controlled in an arbitrary manner, consistent with the mechanics of moving a needle within a patient.

The path of the needle may be monitored by the fluoroscopic images, by magnetic sensors, or by ultrasonic sensors. When the path of the needle is seen to deviate from the desired direction and tip position, the needle direction may be corrected. In addition, a new path between the needle tip and the puncture site may be computed and displayed on the 3D and fluoroscopic images to aid in the needle guidance.

Herein, for convenience in presentation, the medical device being used may be called a needle or a catheter, however any medical device capable of being introduced subcutaneously or through a bodily orifice may be guided in this manner. Thus the use of the term needle, or the description of a specific organ or body structure, should not be considered as suggesting a limitation on the procedures which may be carried out by using this apparatus, computer software product and method. The apparatus and methods described herein may also be used for guiding devices inside of objects or volumes where direct observation of the device is not practical.

In an aspect, a data set suitable for reconstruction into a 3D volumetric rendering may be obtained, for example, by one or more of a CT, PET, SPEC, or MR (magnetic resonance imager) in a preoperative state, or by a C-arm device capable of producing CT-like images in a preoperative or interoperative state, or any other device which produces radiographic images which may be reconstructed into a 3D volumetric image, or into sectioned images showing 3-dimensional structure. The term radiographic images is taken in a broad sense, and may include images taken using other than ionizing radiation, such as with ultrasound devices, MRI, or any device having such capability that now exists or may subsequently be developed. Images may be obtained with and without contrast media, as determined by the medical personnel.

The images obtained for the 3D data set may be referenced to a coordinate system that may be movable with, or associated with the patient, so that the patient may be located with respect to an origin of such coordinate system. If other imaging devices are used, the imaging local coordinate systems of the other imaging devices may be registered with respect to the 3D data set, by any known registration technique including image fusion. As such, images obtained by other imaging devices may be overlaid on or fused with the 3D representation.

During the course of the procedure, intraoperative data may be obtained by, for example a C-arm X-ray device capable of producing a 3D image data set, or capable of producing a fluoroscopic image, angiographic image, or the like. Other devices such as ultrasound may be used, and magnetic and other sensors used to track the position of medical devices. Each of these devices has a local coordinate system, which may be related to the coordinate system of the 3D image data set by physical or computational techniques and methods, as have been described or are otherwise known in the art.

In an aspect, a DynaCT, available from Siemens AG (Munich, Germany), which is a C-arm X-ray imaging modality, may be used to obtain a 3D data set, intra- or pre-operatively, and fluoroscopic or angiographic data obtained a part of the medical procedure. In this instance, the registration of the coordinate axes may arise from the use of the same imaging modality to obtain all of the image data. As mentioned above, this is not necessary as there exist many methods of registration of data obtained from multiple imaging modalities.

The C-arm X-ray system may be mounted on a robotic stand, and the patient support structure may also be robotically mounted, so as to increase the flexibility and precision of orienting the patient with respect to the sensors, life support, sensing, and treatment equipment.

A needle or other medical device introduced into the field of view of a fluoroscopic imaging modality may be viewed from a plurality of directions. When the device is viewed from two or more different angles, the position in space of a feature may be determined. Generally the accuracy is improved when the images are taken from orientations substantially orthogonal to each other, and with an aspect such that the projection of the needle in each of the two fluoroscopic images is maximized. Such an orientation may be determined by the experience of the operating personnel, or be computed based on the approximate geometry of the patient and the needle.

With the needle in a stationary position, the tip of the needle may be identified on each of the fluoroscopic images, thus defining a single point in the volume of the patient. This coordinate location may be related to the coordinate system of the 3D data so that the position of the needle tip may be displayed along with the previously obtained 3D data. The position may be displayed as a small dot or icon, or a more realistic image projected into the 3D image so as to show the orientation of the needle. The viewing direction of the 3D image may be altered so as to aid in interpretation of the composite image, and to visualize the path of the needle to a destination site, which may be a planned puncture area.

In an aspect, the orientation direction of the needle may be determined by locating a second distinctive structure on the treatment apparatus in each of the views of the needle so as to define two points in space along the length of the needle. The combination of multiple views of the needle provides for the determination of the location of the tip of the needle and the orientation direction of the needle.

Alternatively, the direction of the needle may be ascertained by determining the position of the needle tip at two successive locations of the needle tip. That is, the location of the needle tip may be determined as described above, being the location of the needle at a first time. The needle may be linearly advanced a small distance, say 5 mm, and the location of the needle tip determined a second time. The line joining the two determinations of needle tip location defines the direction of orientation of the needle. The positions may be determined using any of the other sensors previously described, performing a similar function.

As the needle is moved, either manually or by robotic device, additional fluoroscopic images are obtained, and the position of the needle re-determined. The guidance of the needle may be altered if the path taken by is seen not to conform to a desired path.

The desired path may be determined with respect to the object of the procedure. For example, in a biopsy, the diagnostic imaging modality, such a MRI or CT may be used to identify a suspected tumor which is the object of the biopsy. The location of the object is designated in the 3-D image set as a point in Cartesian space. When the needle is introduced into the image space, the location of the needle tip, and perhaps the direction of the needle is determined, and located in the same coordinate system. The location of the object and the location of the needle tip may then be joined by a computed line or vector, which may also be displayed for guidance purposes. Where a direction of the needle is determined, a plurality of projections of the needle may be used to visualize the appropriate path.

The selection of the specific guidance approach may be dependent on the type of medical procedure being performed, the location of the object in the patient body, and the specific capabilities of the diagnostic and treatment equipment available at the medical facility.

Figure 1A:
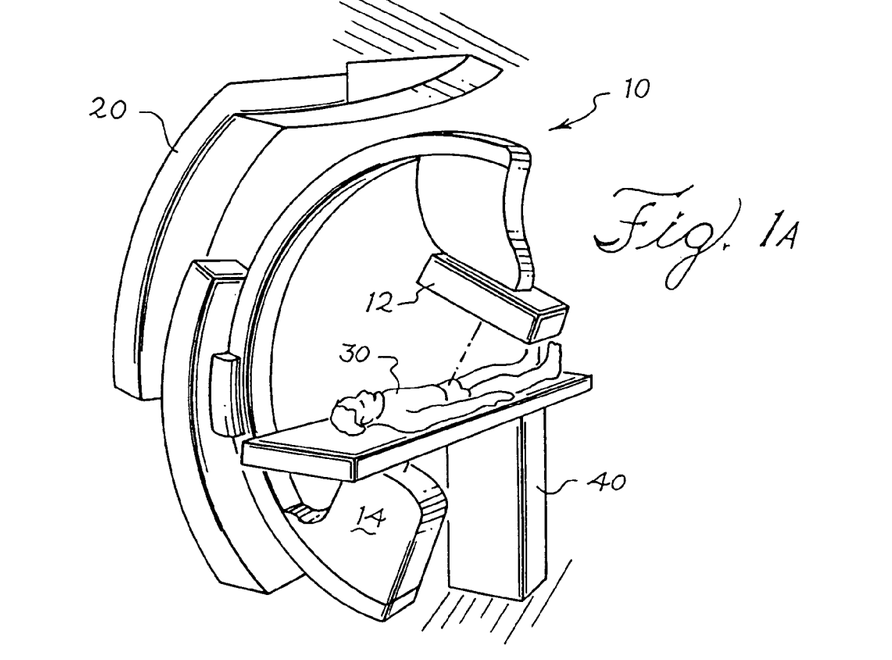
Figure 1B:
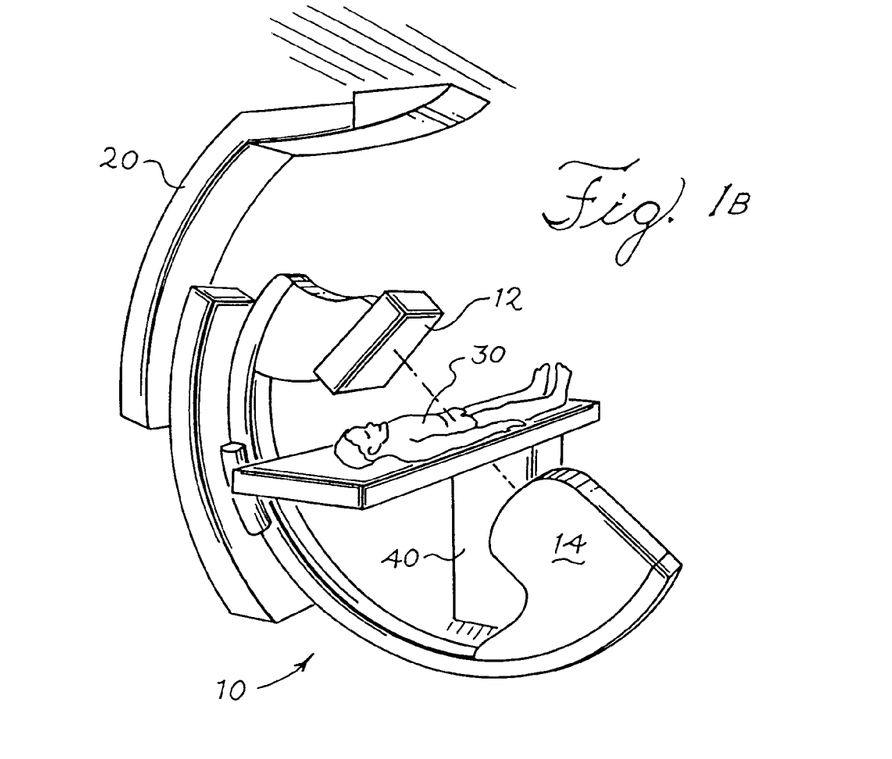

In an example, shown in FIG. 1A, a C-arm X-ray device 10 is mounted to a robot 20 so as to be positionable with respect to a patient support table 30 (the patient is not shown, for clarity). The patient support table 30 may be mounted to the floor by a stand or a robot 40. A dashed line extending between the radiation source 14 and a flat panel detector 12 indicates the central axis of a radiation beam. FIG. 1B shows the same apparatus, repositioned by the robot 40 so that another image, from a direction approximately orthogonal to the first position may be obtained. Such images may be projection radiographic images, and may also be fluoroscopic or angiographic images. The same C-arm X-ray device 10 may be rotated substantially continuously about an axis perpendicular to the C-arm, and a sequence of radiographic image data obtained and processed to form CT-like images. The CT-like images may permit volumetric renderings or cross sectional images to be obtained and manipulated as is known in the art. In this example, the same device is used to obtain the projection radiographic images and the CT-like images, and thus the coordinate systems of the image data are registered with respect to each other. Where different devices are used for the radiographic and CT images, a physical or image fusion means may be used to register the coordinate systems.

Figure 2:
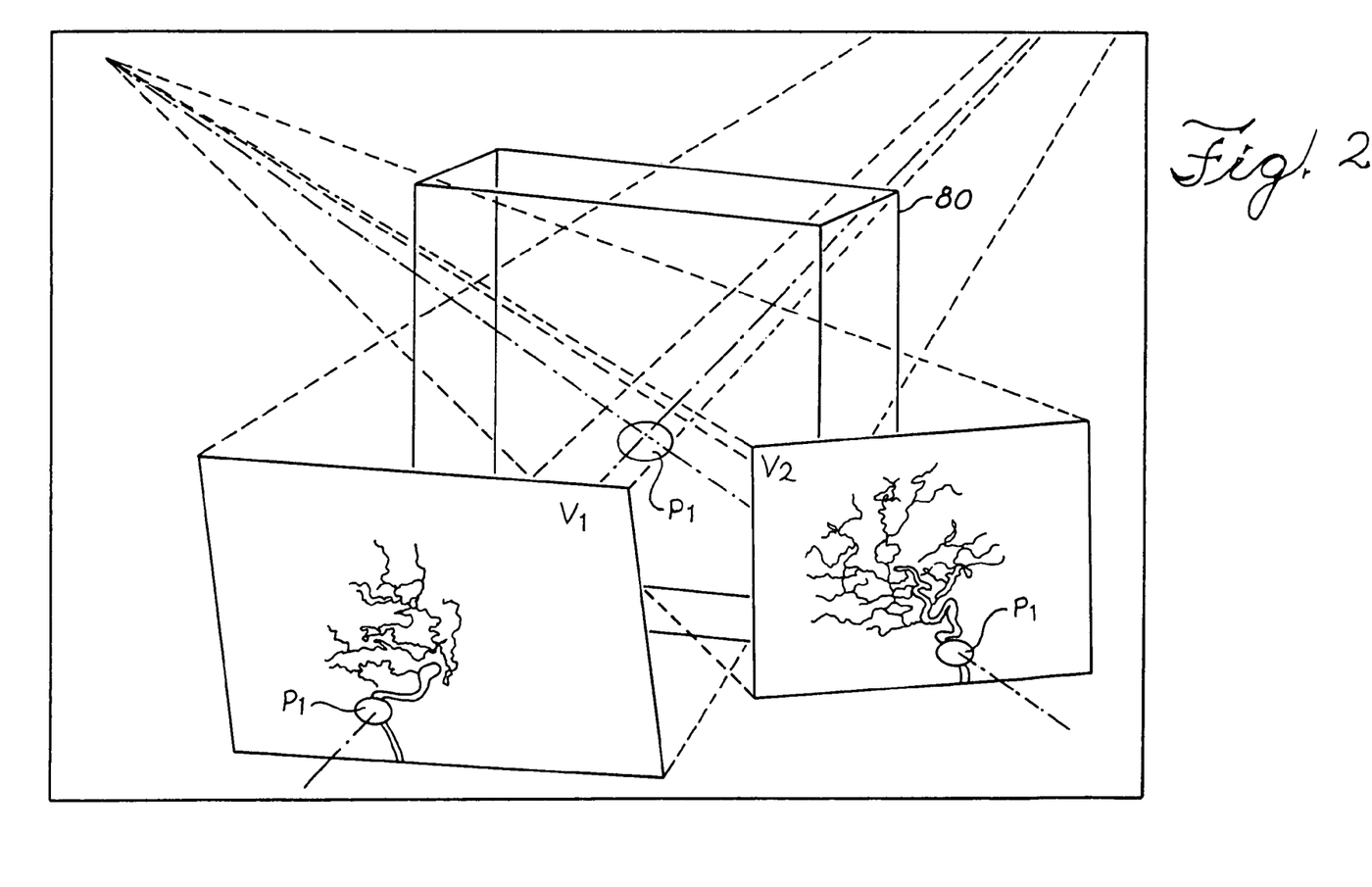
FIG. 2 is a perspective view showing two radiographs taken with the configuration of FIG. 1, where a feature is identified and projected into a 3-dimensional volume.
Figure 3:
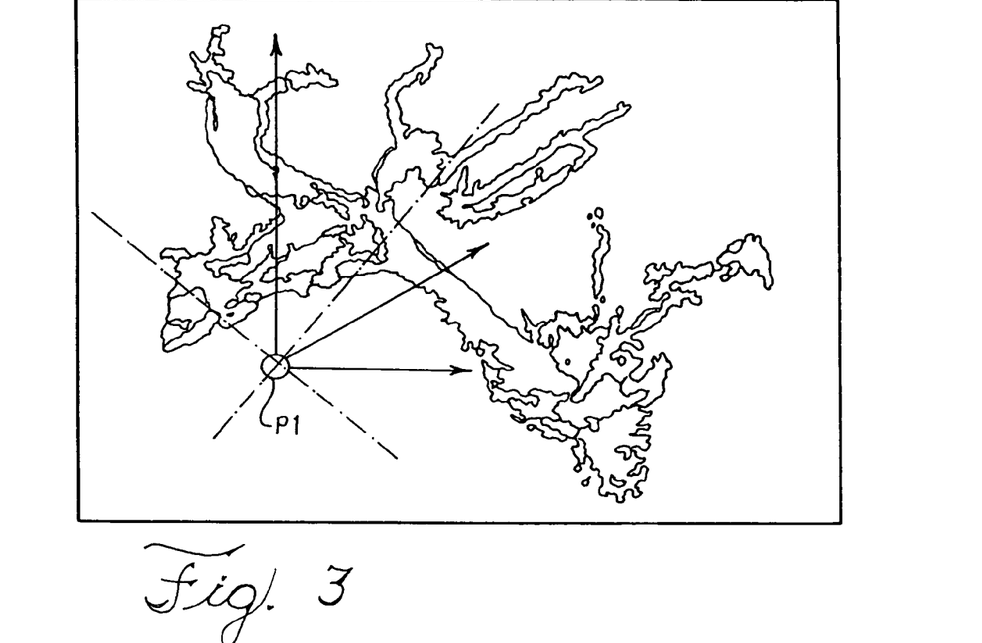
FIG. 3 shows the location of a feature with respect to a 3-dimensional image corresponding to the 2-dimensional images of FIG. 2.

When a medical device, such as a catheter, is introduced into the patient, either by a percutaneous procedure, or through a bodily orifice, two radiographic images may be used to locate a distinguishing feature of the catheter with respect to the three-dimensional volume of the CT-like image. FIG. 2 shows this process schematically. For example, a tip P1 of the catheter may be identified in each of two substantially orthogonal radiographic views (V1, V2). Using the geometry of the C-arm X-ray device, and the known locations of the C-arm device 10 at the time the views V1 and V2 were obtained, the location of the catheter tip in a three-dimensional coordinate system may be computed. In this example, the location P1 is within a volume 80, shown schematically in FIG. 3 as a rectangular parallepiped, which may also have been imaged by the CT-like process. As such, the position of the catheter tip may be displayed in a three-dimensional rendering of the patient body as shown in FIG. 3.

Figure 4:
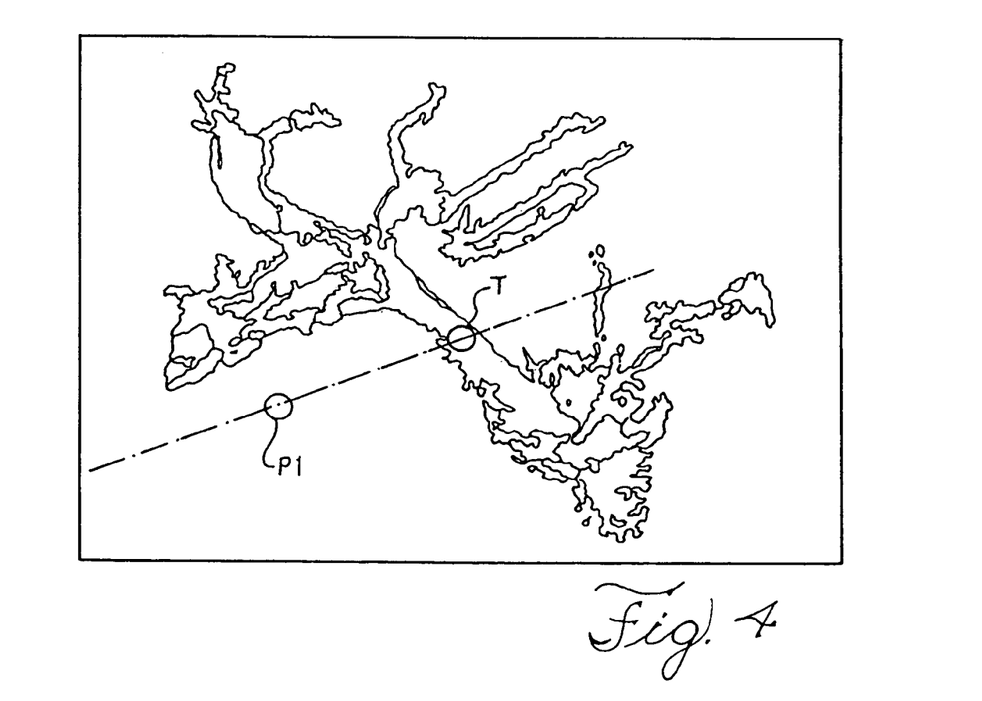
FIG. 4 shows the image of FIG. 3, where a position of a target is also identified.

The medical team may then use the radiographic and CT-like images to identify a target area T, which may be, for example a tumor, or other body structure so as to be able to visualize the relationship between the catheter tip and the target T, as shown in FIG. 4.

Figure 5:
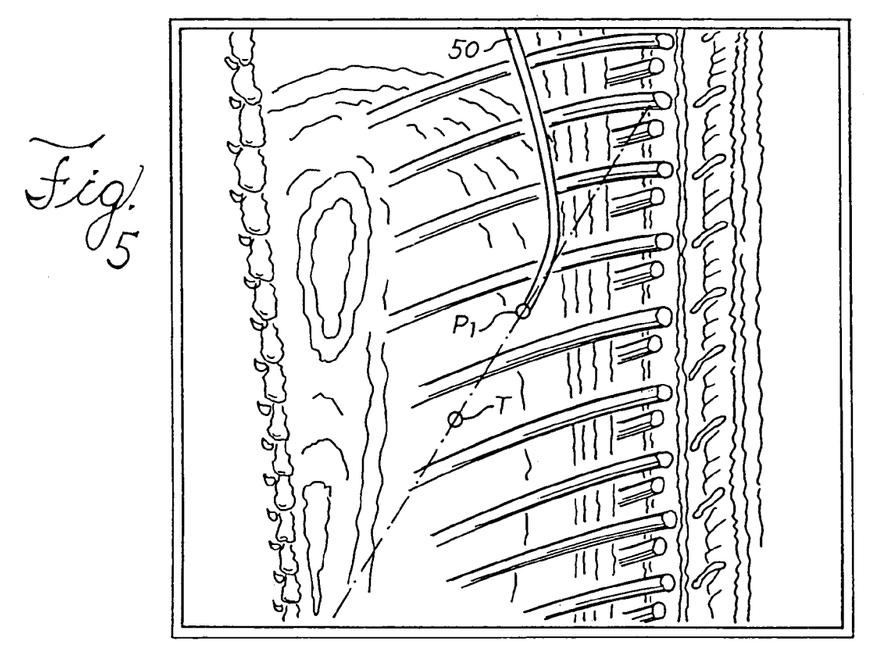
FIG. 5 is a fluoroscopic radiograph where the position of the feature and target of FIG. 4 are shown along with the projection of a vector passing through the location of the feature and the target.

As each of the locations P1 and T are located in the same coordinate system, a vector may be computed defining the linear path between the two locations. The vector may be projected onto a radiographic image, such as shown in FIG. 5. The image shows an overlay of the icons for P1 and T, and a line connecting the two. An image of a medical device which, in this example, is a TIPS needle 50 may be seen.

The TIPS procedure is the placement of a transjugular, intrahepatic, portosystemic shunt. The shunt (tube) is placed between the portal vein which carries blood from the intestines to the liver and the hepatic vein which carries blood from the liver back to the heart. The TIPS procedure has been used primarily, but not exclusively, in patients with cirrhosis in which the scar tissue within the liver has blocked the flow of blood passing through the liver from the portal vein to the hepatic vein. TIPS is a non-surgical means of placing a portosystemic shunt. The shunt is passed down the jugular vein in the neck by a radiologist using fluoroscopic guidance. The shunt then is inserted between the portal and hepatic veins within the liver.

Figure 6:
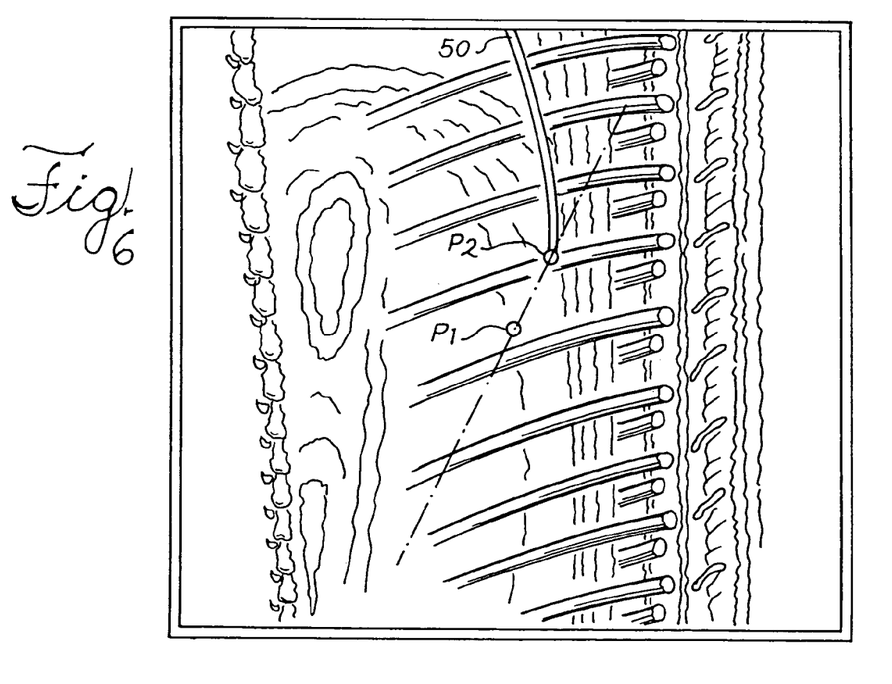
FIG. 6 is a fluoroscopic radiograph where the positions of two features are shown along with a projection of a vector passing through the location of the features.

In another aspect, the location P1 of the needle tip, and another feature P2 of the needle may be identified in the radiographic images, located in the three-dimensional coordinate system including the patient volume, and a vector between the locations P1 and P2 projected onto the fluoroscopic or angiographic image as shown in FIG. 6, being used to guide the needle to the target.

The radiologist or other medical personnel may follow the path of the needle on the radiograph as the procedure is performed, and the course of the needle adjusted if it deviates from the desired path. Further radiographs may be taken to relocate the needle in the three-dimensional coordinate system and compute another vector direction.

In another aspect, a first location P1 of a feature of the medical or other device may be located as described above. The device may be moved a short distance in a linear dimension thereof, and the feature located again. This second determination of a first location P1 may be used in conjunction with the first determination of P1 so as to define a direction of movement of the device. As such this determination may be used as the second position location P2 so as to define the orientation and position of the device A method (100) of guiding a device is disclosed and shown in FIG. 7, the method including, obtaining 3D radiographic image from an imaging modality (200) and introducing a medical or other device into the field of view (150). The method of obtaining the 3D radiographic image may be a CT scanner, a Magnetic Resonance Imaging (MRI) device, a C-arm X-ray device, or the like. The location of a feature of the device is determined (300) and related to the coordinate system of the 3D image (400). The location may be displayed as an icon, or the like, in a 3D image which may be a 3D rendering or a cross section in a selected orientation using data obtained in step 200. The method of determining the location of the feature (300) may be, for example, by the use of a C-arm X-ray device, an ultrasound imager, or a magnetic detector. A second location, which may be an organ, a tumor, other bodily structure, or a second feature on the device may also be identified (700) using one of the 3D image or the location method (300).

Figure 7:
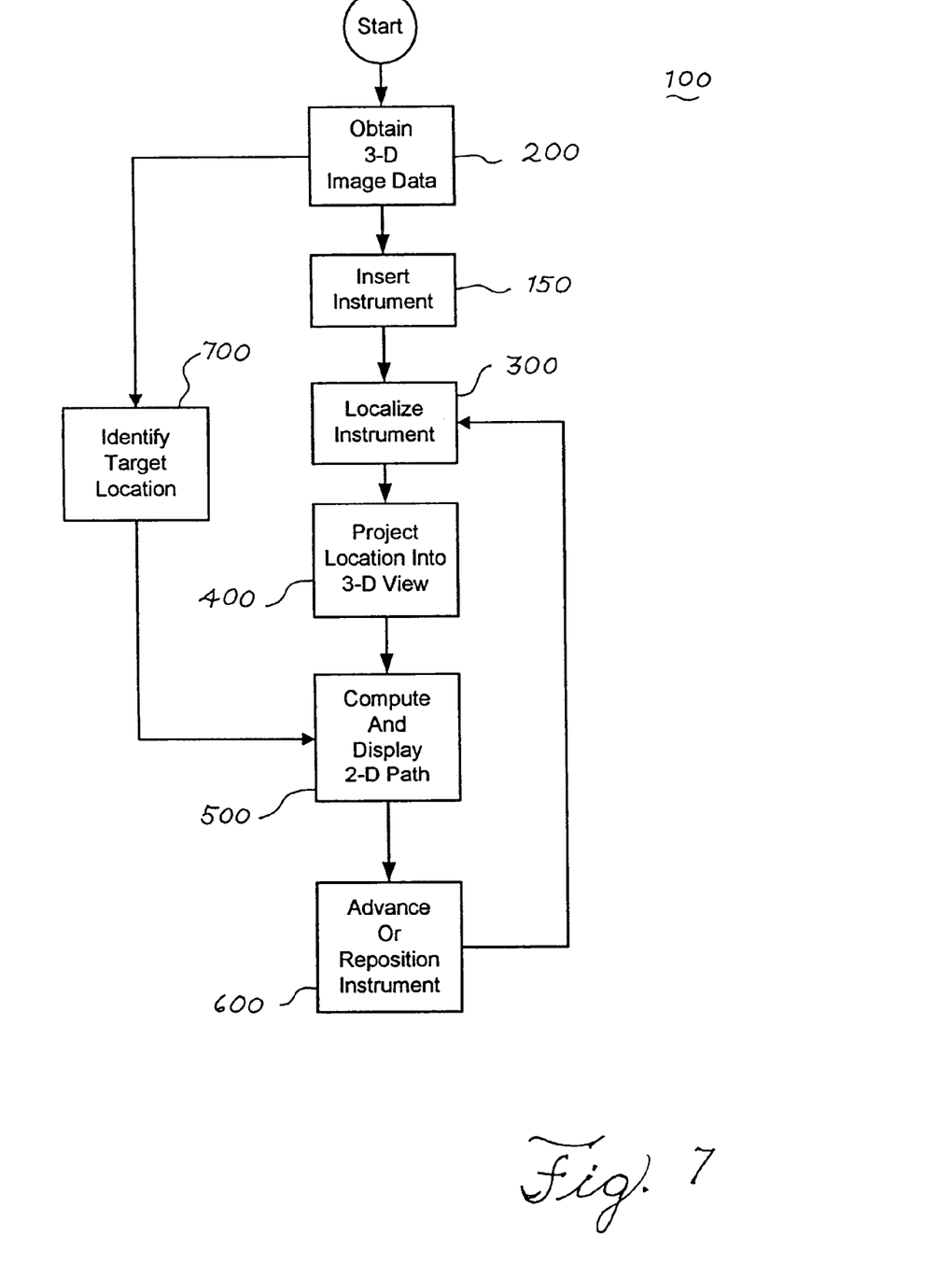
FIG. 7 is a flow chart of a method of guiding an instrument in a patient body.

The two locations may be used to define the vector joining the two, and the vector may be projected beyond each of the locations. The locations and the vector may be projected into the plane of one or more radiographic projection images (500), which may be a fluoroscopic or angiographic image. The medical personnel may then move the device so as to, for example, advance the device generally along the line of the vector (600). The localization procedure (300) may be repeated as necessary to assist in the guidance of the device.

Figure 8:
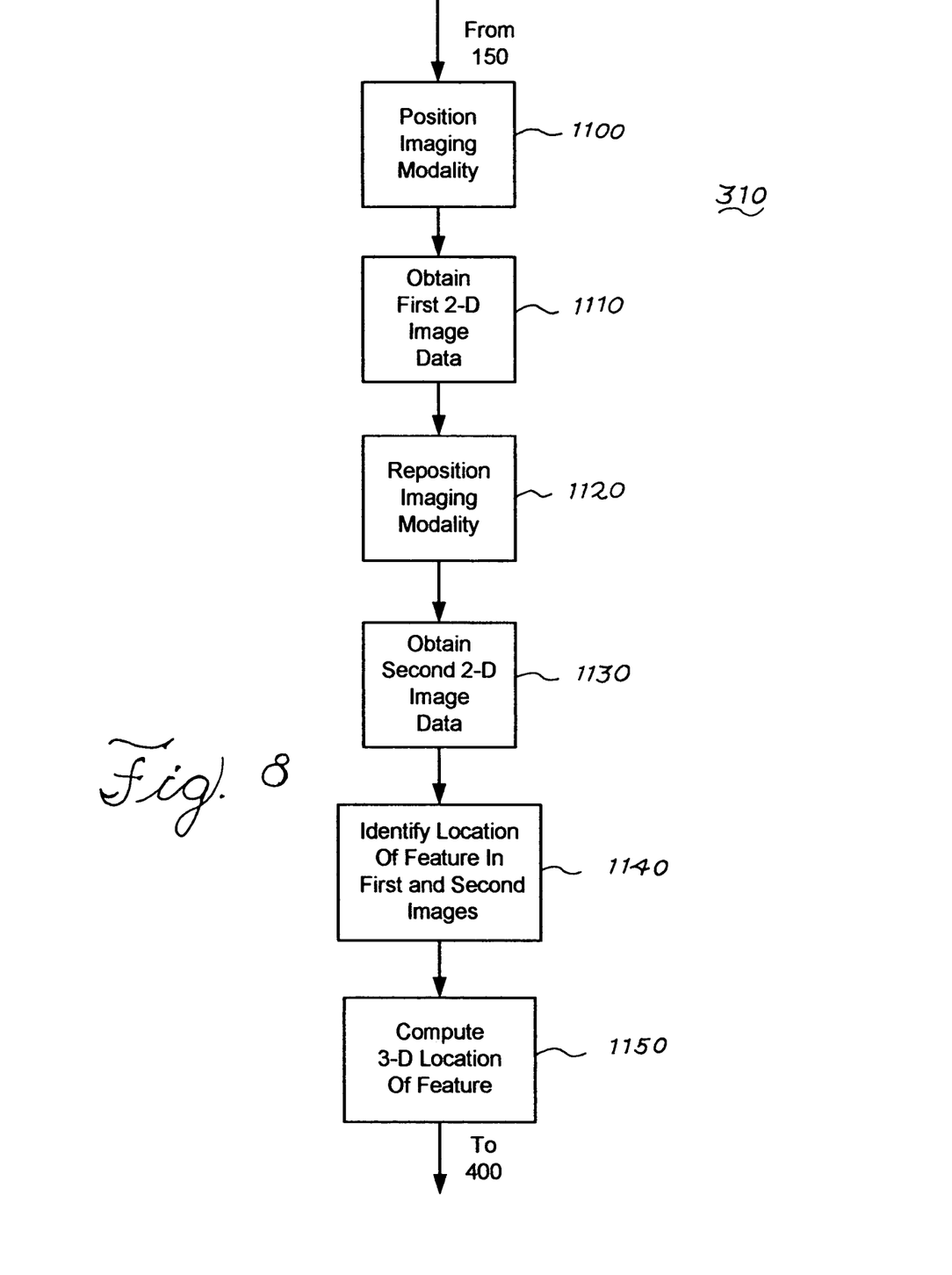
FIG. 8 is a flow chart of a detail of the method of FIG. 7 for a method determining the location of a feature of the instrument.

In an aspect, localizing the device (300) may be performed as shown in FIG. 8 as 310. After the device is inserted (150) into the field of view of the device used for the localization, which may be an imaging modality such as the C-arm X-ray device, shown in FIG. 1, a projection radiographic image is obtained (1110). The imaging modality is repositioned (1120) so that another view may be obtained (1130). In an aspect, this second view may be substantially orthogonal to the first view. The orientation may be limited by practical considerations of the location of life support equipment and other apparatus.

A distinctive feature of the device is identified (1140). This feature may be the tip of a needle, a change in diameter, or the like. The location may be determined by an operator viewing the projection radiographic images and designating the location of the feature on each radiograph, or the analysis may be performed automatically taking into account the differing radiographic opacities of the body tissue and the device. The computed position of the feature (1150) may then be obtained in the 3 dimensional coordinate system of the 3D image.

Figure 9:
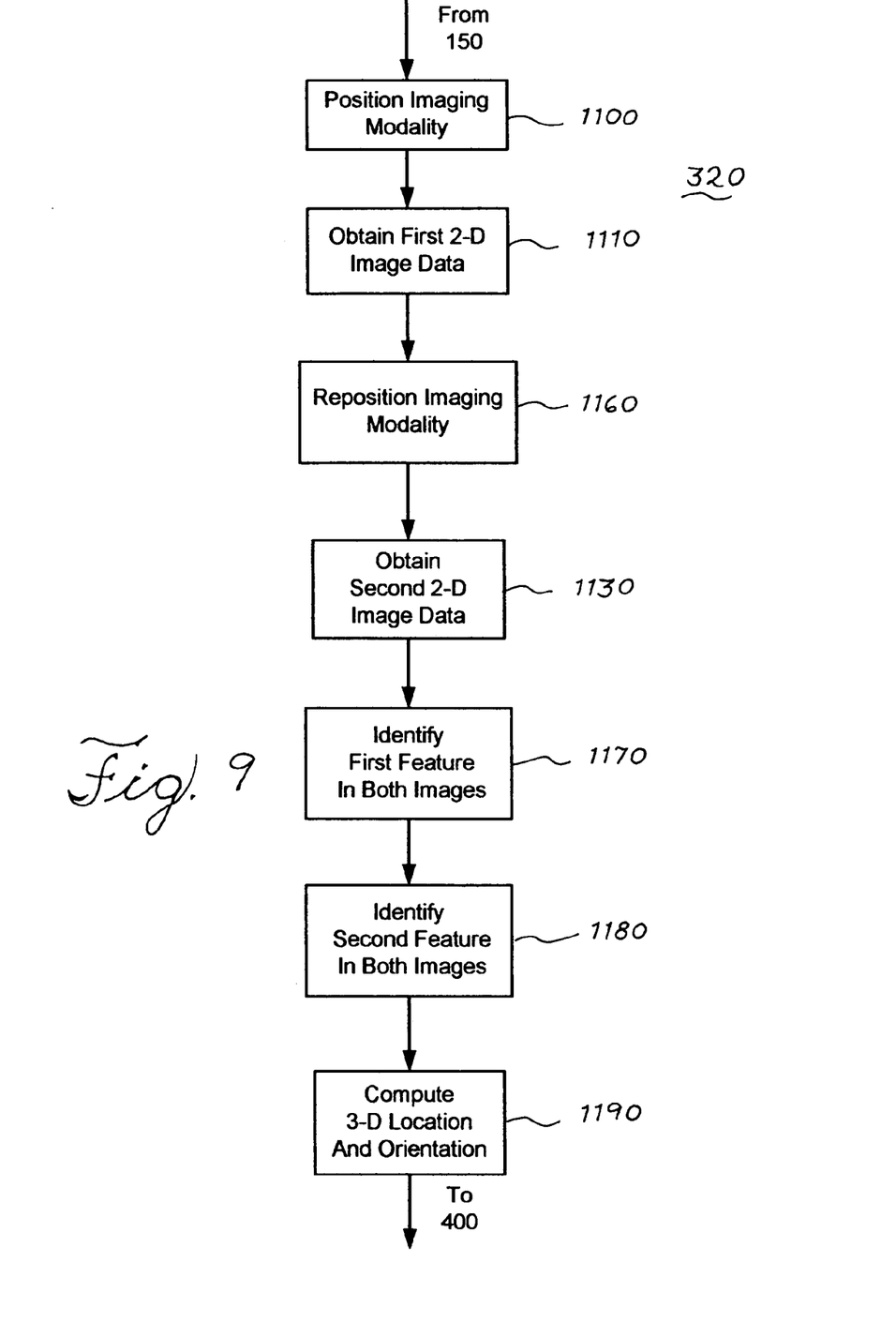
FIG. 9 is a flow chart of a detail of the method of FIG. 7 for a first method of determining the location and orientation direction of an instrument.

In another aspect, the location method may as shown in FIG. 9 as 320. The method is similar to that of 310, and thus only the salient differences are described. The imaging modality is positioned and a first radiograph is obtained (1110). The imaging modality is repositioned and a second radiograph is obtained. A first location and a second location on the device is determined in the first radiographic image (1170), and a first and a second location on the device is determined on the second radiographic image (1180). The two sets of locations, that is the two first locations and the two second locations are used to determine two three dimensional positions of the device (1190). In the case of a slim device such as a needle, the two locations determine both the position and the orientation of the device in the 3-dimensional coordinate system related to the image obtained by the 3D imaging modality.

Figure 10:
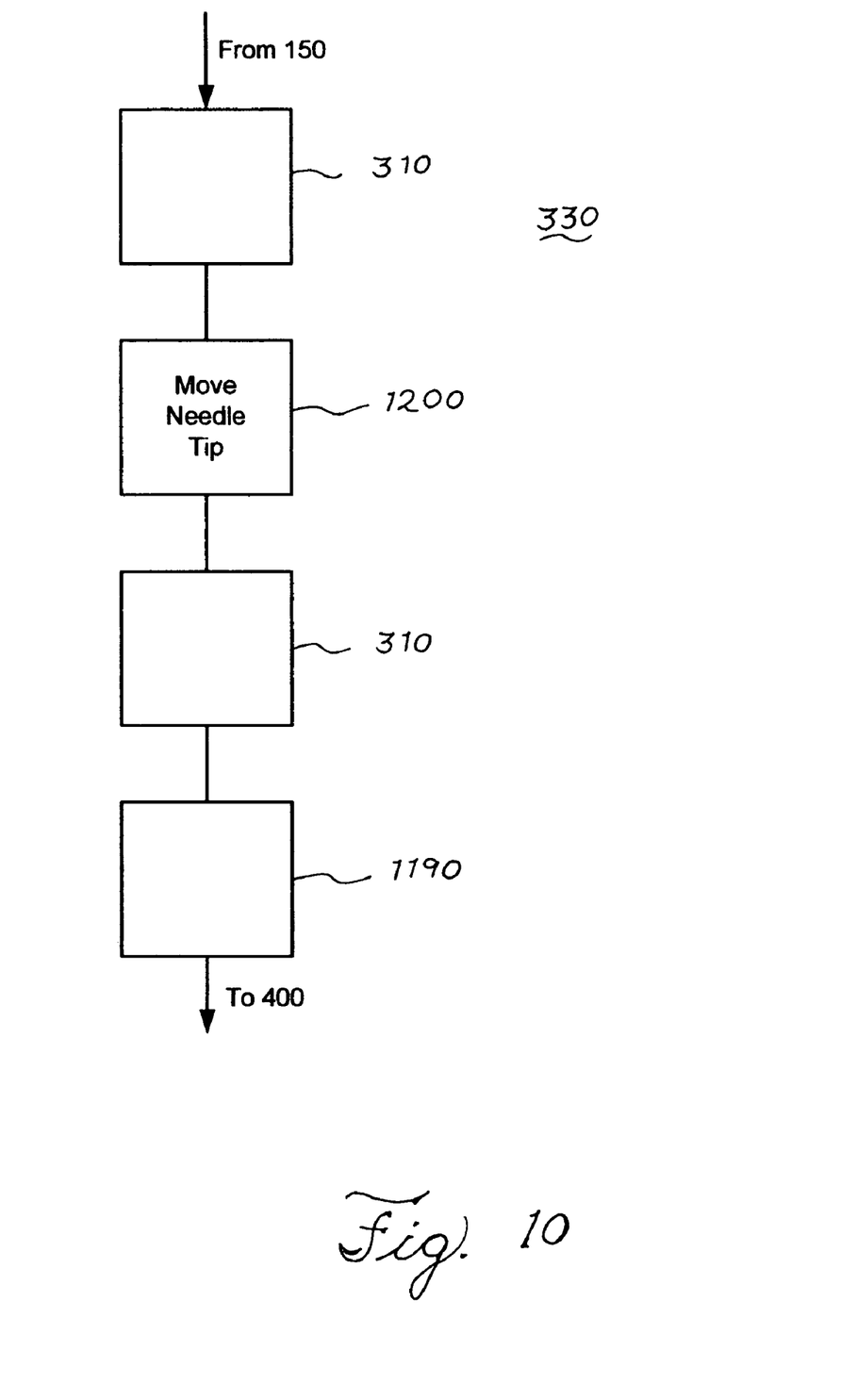
FIG. 10 is a flow chart of a detail of the method of FIG. 7 for a second method of determining the location and orientation direction of an instrument.

In yet another aspect, the location method may as shown in FIG. 10 as 330. The location procedure may be performed for a feature of the device according to the method 310. This provides a first position location of, for example, the tip of a needle. The needle may be advanced a small distance in a linear manner, along the length direction of the needle, and a second determination of the position of the tip of the needle obtained. The two position locations define the direction of motion of the tip and the location of the tip, and may be used to guide the movement of the needle as described previously.

Figure 11:
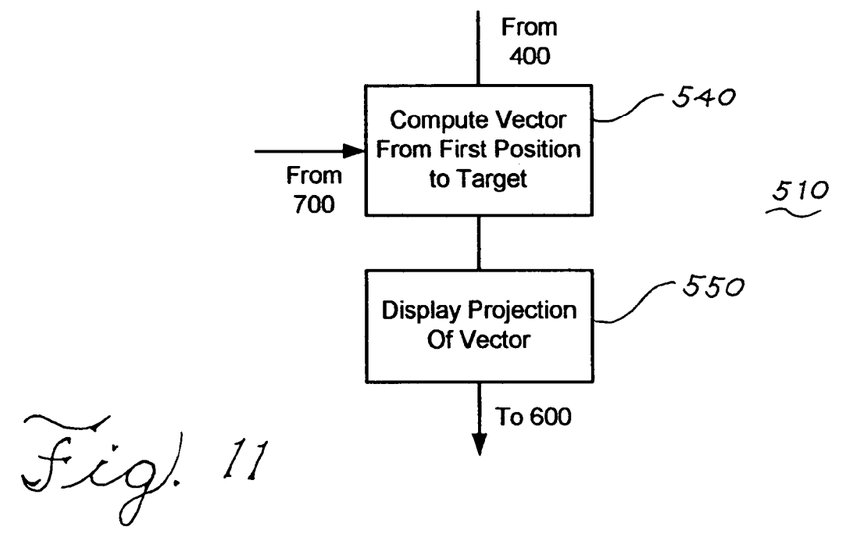
FIG. 11 is a flow chart of a detail of the method of FIG. 7 for a first method of using the position of a target and a position of a feature to guide the medical instrument.

Several strategies may be used for assisting the guidance of device, which may be a needle or a catheter, or the like. In an aspect, shown in FIG. 11, the position of, for example the tip of a needle and a tumor may each be identified. A vector connecting the two positions may be computed (540) and projected into the plane of a radiographic image (550) so that the direction of motion of the needle may be visualized by the medical personnel.

Figure 12:
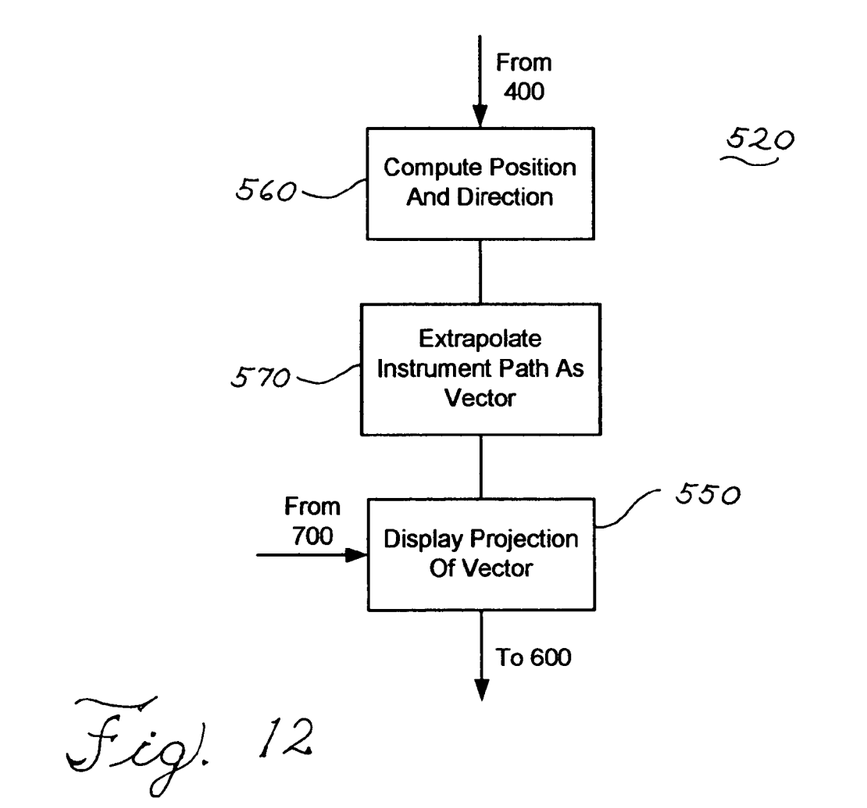
FIG. 12 is a flow chart of a detail of the method of FIG. 7 for a second method of using the position of a target and a position of a feature to guide the medical instrument.

In another aspect, shown in FIG. 12, the position of two features on the needle or catheter may be determined, or the position of the tip before and after movement may be determined so as to determine the position and orientation of the device (560). A vector defined by the orientation of the device may be computed (570) and may project in to a radiographic image (550).

A computer software product is disclosed, the product being embodied by recording the computer software instructions on a machine readable medium. When read from the machine readable medium, or a copy thereof, so as to become executable instructions for the processing unit of a computer device, the instructions configure the computed to perform the method 500 as described above.

The software instructions may be stored as executable computer code on a removable media device for reading by local or remote systems. In other embodiments, the instructions may be stored in a remote location for transfer through a computer network, a local or wide area network, by wireless techniques, or over telephone lines. In yet other embodiments, the instructions are stored within a given computer, system, or device.

The methods disclosed herein have been described and shown with reference to particular steps performed in a particular order; however, it will be understood that these steps may be combined, sub-divided, or reordered to from an equivalent method without departing from the teachings of the present invention. Accordingly, unless specifically indicated herein, the order and grouping of steps is not a limitation of the present invention.

Embodiments of this invention may be implemented in hardware, firmware, software, or any combination thereof, and may include instructions stored on a machine-readable medium, which may be read and executed by one or more processors. In an aspect where a computer or a digital circuit is used, signals may be converted from analog format to a digital representation thereof in an analog-to-digital (A/D) converter, as is known in the art. The choice of location of the A/D conversion will depend on the specific system design.

The instructions for implementing processes may be provided on computer-readable storage media. Computer-readable storage media include various types of volatile and nonvolatile storage media. Such storage media may be memories such as a cache, buffer, RAM, flash, removable media, hard drive or other computer readable storage media. The functions, acts or tasks illustrated in the figures or described herein may be performed in response to one or more sets of instructions stored in or on computer readable storage media. The functions, acts or tasks are independent of the particular type of instruction set, storage media, processor or processing strategy and may be performed by software, hardware, integrated circuits, firmware, micro code and the like, operating alone or in combination. The instructions may be stored on a removable media device for reading by local or remote systems. In other embodiments, the instructions may be stored in a remote location for transfer through a computer network, a local or wide area network or over telephone lines. In yet other embodiments, the instructions are stored within a given computer or system.

Although only a few examples of this invention have been described in detail above, those skilled in the art will readily appreciate that many modifications are possible without materially departing from the novel teachings and advantages of the invention. Accordingly, all such modifications are intended to be included within the scope of this invention as defined in the following claims.

What is claimed is:

1. An apparatus for visualizing the position of an object, comprising:
    a first imaging modality capable of producing projection images from at least two different orientations with respect to the object;
    a second imaging modality capable of producing three-dimensional images of a volume including the object;
    a processor configured to:
        identify a first distinguishing feature of the object in the projection images taken from at least two different orientations;
        identify a first distinguishing feature of the volume in the three-dimensional images;
        compute the three-dimensional location of the first distinguishing feature of the object using the projection images taken from at least two different orientations and the first distinguishing feature of the volume in a three dimensional coordinate system;
        compute a first vector representative of an initial path between the first distinguishing feature of the object and the first distinguishing feature of the volume; and
        display a projection of the first vector on at least one of the three-dimensional images or the projection images; and
    a sensor configured to monitor a position of the first distinguishing feature of the object,
    wherein the processor is further configured to compute a second vector representative of a modified path between the first distinguishing feature of the object and the first distinguishing feature of the volume when the sensor determines that the position of the first distinguishing feature of the object has deviated from the initial path, and
    wherein the processor is further configured to display a projection of the second vector on at least one of the three-dimensional images or the projection images.

2. The apparatus of claim 1, wherein the first imaging modality and the second imaging modality are the same device.

3. The apparatus of claim 1, wherein at least one of the first imaging modality or the second imaging modality is a C-arm X-ray device.

4. The apparatus of claim 3, wherein the C-arm X-ray device is mounted to a robot.

5. The apparatus of claim 3, further comprising a display capable of displaying a fluoroscopic or angiographic image.

6. The apparatus of claim 5, wherein the processor is further configured to determine the three-dimensional location of a second distinguishing feature of the object and to compute a third vector representative of a distance between the locations of one of the first distinguishing features and the second distinguishing feature.

7. The apparatus of claim 6, wherein the third vector and a projection of the third vector are displayed on a fluoroscopic or an angiographic image.

8. The apparatus of claim 1, wherein the coordinate systems of the first imaging modality and the second imaging modality are registered with respect to each other.

9. The apparatus of claim 1, wherein the three-dimensional coordinate system is fixed with respect to a patient.

10. The apparatus of claim 1, wherein the first distinguishing feature of the object is a tip of a needle, and the first distinguishing feature of the volume is a target point on a surface of an organ of a patient.

11. A method of guiding an object in a patient, the method comprising:
    providing a first imaging modality configured to obtain three dimensional radiographic data;
    providing a second imaging modality configured to obtain radiographic images of a patient or portion thereof from at least two orientations, the images of the second imaging modality being registered or registerable with the images of the first imaging modality;
    providing an image display device;
    introducing an object into the field of view of the second imaging modality;
    identifying a first distinguishing feature of the object in at least two radiographic images;
    determining the three-dimensional location of a first position of the first distinguishing feature of the object from projection images taken from the radiographic images of the patient or portion thereof from at least two orientations and determining the location of a first distinguishing feature of the patient in a three-dimensional coordinate system;
    computing a vector between the first position of the first distinguishing feature of the object and the first distinguishing feature of the patient, and displaying the vector on the three dimensional radiographic data or a projection of the vector on a radiographic image;
    moving the first distinguishing feature of the object to a second position;
    determining the three-dimensional location of the second position of the first distinguishing feature of the object from protection images taken from the radiographic images of the patient or portion thereof from at least two orientations;

determining if the three-dimensional location of the second position of the first distinguishing feature of the object lies within a path defined by the vector between the first position of the first distinguishing feature of the object and the first distinguishing feature of the patient; and computing a vector between the second position of the first distinguishing feature of the object and the first distinguishing feature of the patient if it is determined that the second position of the first distinguishing feature of the object lies outside of the path defined by the vector between the first position of the first distinguishing feature of the object and the first distinguishing feature of the patient.

12. The method of claim 11, wherein the first imaging modality and the second imaging modality are the same device.

13. The method of claim 11, wherein the radiographic image produced by the second imaging modality is at least one of a fluoroscopic or an angiographic image.

14. The method of claim 11, further comprising automatically adjusting an orientation of the object when it is determined that the second position of the first distinguishing feature of the object lies outside of the path defined by the vector between the first distinguishing feature of the object and the first distinguishing feature of the patient.

15. A software product, recorded on a non-transitory machine readable media, that configures a computer to perform a method of visualizing guiding an object, the method comprising:

obtaining three-dimensional imaging data of at least a portion of a patient;

obtaining projection radiographic images of a volume including an object from at least two differing orientations;

identifying a first distinguishing feature of an object by one of displaying the radiographs or by automated image analysis;

identifying a target location in the patient; and determining the three-dimensional location of the first distinguishing feature of the object from the projection radiographic images of the volume including the object from at least two different orientations;

computing a vector between the first distinguishing feature and the target location in the patient, and computing a projection of the vector on a fluoroscopic or radiographic image;

moving the object along a linear dimension thereof;

identifying a second distinguishing feature of the object, the second distinguishing feature being a new position of the object resulting from moving the object;

determining if the second distinguishing feature of the object has deviated from a path defined by the vector between the first distinguishing feature of the object and the target location in the patient; and computing a vector between the second distinguishing feature of the object and the target location in the patient when it is determined that the second distinguishing feature of the object has deviated from the path defined by the vector between the first distinguishing feature of the object and the target location in the patient.

16. The software product of claim 15, wherein the first distinguishing feature of the object is a tip of a needle and the target location in the patient is a target point on a surface of an organ of a patient, and further comprising adjusting the orientation of the tip of the needle when it is determined that the second distinguishing feature of the object has deviated from the path defined by the vector between the first distinguishing feature of the object and the target location in the patient.

17. The software product of claim 15, further comprising automatically adjusting an orientation of the object when it is determined that the second distinguishing feature of the object has deviated from the path defined by the vector between the first distinguishing feature of the object and the target location in the patient.

* * * * *